United States Patent [19]

Holzhauer et al.

[11] Patent Number: 5,262,560

[45] Date of Patent: Nov. 16, 1993

[54] PROCESS FOR PREPARING PURIFIED DIMETHYL NAPHTHALENEDICARBOXYLATE

[75] Inventors: Juergen K. Holzhauer, Naperville; David A. Young, Warrenville; Martin A. Zeitlin, Naperville; Paul K. Behrens, Warrenville, all of Ill.

[73] Assignee: Amoco Corporation, Chicago, Ill.

[21] Appl. No.: 708,500

[22] Filed: May 31, 1991

[51] Int. Cl.⁵ ............................................. C07C 67/48
[52] U.S. Cl. ............................................ 560/78; 560/100
[58] Field of Search ................................... 560/78, 100

[56] References Cited

U.S. PATENT DOCUMENTS

| | | | |
|---|---|---|---|
| 3,037,048 | 5/1962 | Lotz et al. | 560/78 |
| 3,485,867 | 12/1969 | Jackson | 560/78 |
| 4,048,021 | 9/1977 | Takamoto et al. | 560/80 |
| 4,230,882 | 10/1980 | Seko et al. | 562/416 |
| 5,095,135 | 3/1992 | Yamada et al. | 560/100 |

FOREIGN PATENT DOCUMENTS

| | | |
|---|---|---|
| 0450621 | 10/1991 | European Pat. Off. . |
| 50-111055 | 9/1975 | Japan . |
| 50-111056 | 9/1975 | Japan . |
| 50-160247 | 12/1975 | Japan . |

Primary Examiner—José G. Dees
Assistant Examiner—Joseph M. Conrad
Attorney, Agent, or Firm—Thomas E. Nemo; Wallace L. Oliver; Frank J. Sroka

[57] ABSTRACT

A process for preparing purified dimethyl-2,6-naphthalenedicarboxylate by the esterification of 2,6-naphthalenedicarboxylic acid is disclosed and which process provides for the efficient removal of the mono methyl ester of 2,6-naphthalenedicarboxylic acid produced during the esterification reaction.

20 Claims, No Drawings

PROCESS FOR PREPARING PURIFIED DIMETHYL NAPHTHALENEDICARBOXYLATE

FIELD OF THE INVENTION

This invention relates generally to a process for preparing purified dimethyl naphthalenedicarboxylate containing low levels of organic impurities, low color, and low levels of particulate contaminants. More particularly, this invention relates to a process for preparing purified dimethyl-2,6-naphthalenedicarboxylate by the esterification of 2,6-naphthalenedicarboxylic acid with methanol, and which process provides for the efficient removal of the mono methyl ester of 2,6-naphthalenedicarboxylic acid produced during the esterification reaction.

BACKGROUND OF THE INVENTION

The diesters of naphthalenedicarboxylic acids are useful for preparing a variety of polymeric materials such as polyesters or polyamides. One particularly useful diester is dimethyl-2,6-naphthalenedicarboxylate (DM-2,6-NDC). Dimethyl-2,6-naphthalenedicarboxylate, for example, can be condensed with ethylene glycol to form poly(ethylene-2,6-naphthalate) (PEN), a high performance polyester material. Fibers and films made from PEN have considerably improved strength and superior thermal properties relative to, for example, poly(ethyleneterephthalate). For this reason, PEN is an exceptional material for preparing commercial articles such as thin films which can be used, for example, in the manufacture of magnetic recording tape and electronic components. Additionally, because of its superior resistance to gas diffusion, and particularly to the diffusion of carbon dioxide, oxygen and water vapor, films made from PEN are useful for manufacturing food containers, especially the so-called "hot fill" food containers. PEN can also be used to prepare high strength fibers useful for the manufacture of, for example, tire cord.

In order to prepare high quality PEN suitable for commercial use, it is necessary to start with purified DM-2,6-NDC. The purified DM-2,6-NDC must be low in color, substantially free of organic and inorganic impurities, and low in particulate matter.

DM-2,6-NDC is most readily prepared by the esterification of 2,6-naphthalenedicarboxylic acid (2,6-NDA) with methanol. The 2,6-NDA is conveniently prepared by the liquid phase, heavy metal catalyzed oxidation of a 2,6-dialkyl- or 2-alkyl-6-acyl naphthalene compound using molecular oxygen as the source of oxygen for the oxidation reaction. During this oxidation reaction impurities such as 6-formyl-2-naphthoic acid (FNA), trimellitic acid (TMLA) and, when a bromine oxidation promoter is used, various brominated compounds are produced. Although in some instances it would be desirable to use 2,6-NDA directly for the preparation of PEN, however, because of its high melting point (>300° C. with decomposition) and extremely low solubility in ordinary solvents, 2,6-NDA is extremely difficult to purify to acceptable levels by standard purification techniques such as distillation and recrystallization. These difficulties in purifying 2,6-NDA are partially overcome by converting 2,6-NDA to its dimethyl ester, DM-2,6-NDC. DM-2,6-NDC can be distilled and it can be recrystallized from solvents such as methanol or from one or more aromatic solvents. However, even though DM-2,6-NDC can be purified by treatments such as distillation or recrystallization, purifying DM-2,6-NDC to a purity acceptable for use in the aforementioned manufactured articles remains a problem in the art. For example, the FNA produced during the oxidation of dialkylnaphthalene is incorporated (as a methyl ester) into DM-2,6-NDC during the esterification of 2,6-NDA and is very difficult to remove or reduce to acceptable low levels. Oxidation catalyst metals such as cobalt and manganese when used with a bromine promotor for the preparation of 2,6-NDA are also typically carried over into the esterification reaction as impurities. This is because a certain amount of the oxidation catalyst metal is complexed tightly to TMLA and other oxidation by-products and is not removed in the oxidation mother liquor when the oxidation mother liquor is separated from the solid 2,6-NDA. Catalyst metals cause problems in the downstream operations used for purifying the DM-2,6-NDC by, for example, causing a thickening of the distillation bottoms and plugging of the distillation column.

Additionally, during the esterification reaction, the mono methyl ester of 2,6-naphthalene dicarboxylic acid, hereinafter referred to as mono-methyl-2,6-naphthalenedicarboxylate (MM-2,6-NDC), is produced and it must be removed from the DM-2,6-NDC. Furthermore, it is highly desirable to remove most of the MM-2,6-NDC from the DM-2,6-NDC before it is distilled. Otherwise, because it is a high melting solid, it causes an excessively large amount of distillation bottoms, and it can precipitate in and foul the distillation apparatus. The ratio of methanol to 2,6-NDA in the esterification reaction determines the amount of MM-2,6-NDC produced. When the ratio is high, for example greater than 10:1 by weight, respectively, only a small amount of MM-2,6-NDC is formed. However, when a low ratio of methanol to 2,6-NDA is used, for example 4:1, as much as 6 to 10 weight percent of the esterification product is MM-2,6-NDC. Using high ratios of methanol to 2,6-NDA in order to avoid the formation of MM-2,6-NDC is not, however, desirable for a large, commercial-scale operation. High ratios of methanol to 2,6-NDA necessitate using a large esterification reactor for a given throughput of product. Additionally, by using a high ratio of methanol to 2,6-NDA, large quantities of methanol must be recycled and the loss of DM-2,6-NDC is greater due to the amount of DM-2,6-NDC remaining in solution in the extra methanol.

The present invention allows for the use of low ratios of methanol to 2,6-NDA in the esterification by providing for the effective separation of MM-2,6-NDC from DM-2,6-NDC. Furthermore, in the process of this invention, the separated MM-2,6-NDC is relatively free of undesirable impurities and it is therefore recyclable to the esterification reactor where it is converted to DM-2,6-NDC, resulting in no loss of valuable product.

Finally, especially for applications where the DM-2,6-NDC will be used for making PEN for very thin films, particulate contamination in the DM-2,6-NDC must be eliminated or reduced to very low levels. These particulate impurities, which range in size down to below 1.5 microns, can arise from a variety of sources. For example, they may be either oxidation catalyst particles or, if used, esterification catalyst particles. They may also be derived from filtering and drying operations where DM-2,6-NDC is dissolved in a solvent, recrystallized, separated from the recrystallization mother liquor by filtration and dried to remove excess solvent. Inevitably, particulates contaminate the DM- 2,6-NDC product in these processes. Regardless of the source, particulate contamination in the DM-2,6-NDC product is undesirable.

Processes for manufacturing and purifying DM-2,6-NDC have been disclosed. Japanese Kokai Patent No. Sho 50-116461, for example, discloses a process for preparing DM-2,6-NDC wherein crude DM-2,6-NDC from the esterification of 2,6-NDA with methanol is distilled and then crystallized from methanol. This process is taught as being superior to one where the crystallization from methanol precedes the distillation. However, the Japanese Kokai Patent No. Sho 50-116461, although disclosing a process for preparing DM-2,6-NDC from 2,6-NDA by reaction with methanol, does not disclose the advantages of using low ratios of methanol to 2,6-NDA. It also does not teach a suitable means for removing large amounts of MM-2,6-NDC from DM-2,6-NDC. Additionally, this Kokai patent teaches that it is essential to recrystallize the DM-2,6-NDC subsequent to a distillation step in order to prepare DM-2,6-NDC with acceptable color. However, this order of the purification steps does not provide for low levels of particulates in the final DM-2,6-NDC product that is required for some of the aforementioned uses of DM-2,6-NDC.

The art needs a process for the large-scale preparation of DM-2,6-NDC having suitably low color and low levels of impurities such as the methyl ester of FNA, bromine containing impurities and, especially, MM-2,6-NDC and particulate contaminants. The art also needs a process for efficiently removing MM-2,6-NDC from DM-2,6-NDC so that reduced ratios of methanol to 2,6-NDA can be used in the esterification reaction. The present invention provides such a process.

SUMMARY OF THE INVENTION

Provided is a process for preparing purified dimethyl-2,6-naphthalene dicarboxylate from 2,6-naphthalenedicarboxylic acid, which process comprises:

a) reacting in a suitable reaction zone the 2,6-naphthalenedicarboxylic acid with methanol to form a reaction mixture comprising dissolved dimethyl-2,6-naphthalenedicarboxylate and mono-methyl-2,6-naphthalenedicarboxylate; b) crystallizing a major portion of the dissolved dimethyl-2,6-naphthalenedicarboxylate and mono-methyl-2,6-naphthalenedicarboxylate by cooling the reaction mixture to a temperature not greater than about 40° C.; c) partitioning reaction mixture mother liquor from crystallized dimethyl-2,6-naphthalenedicarboxylate and mono-methyl-2,6-naphthalenedicarboxylate; d) heating partitioned dimethyl-2,6-naphthalenedicarboxylate and mono-methyl-2,6-naphthalenedicarboxylate in a recrystallization solvent at a temperature sufficient to dissolve at least a portion of the dimethyl-2,6-naphthalenedicarboxylate and substantially all of the mono-methyl-2,6-naphthalenedicarboxylate; e) recrystallizing dimethyl-2,6-naphthalenedicarboxylate dissolved in the recrystallization solvent at a temperature to recrystallize the dimethyl-2,6-naphthalenedicarboxylate while maintaining a major portion of the mono-methyl-2,6-naphthalenedicarboxylate in recrystallization mother liquor; f) partitioning recrystallized dimethyl-2,6-naphthalenedicarboxylate from the recrystallization mother liquor; and, preferably, g) vacuum distilling the recrystallized dimethyl-2,6-naphthalenedicarboxylate to form highly purified dimethyl-2,6-naphthalenedicarboxylate having low color, low levels of mono-methyl-2,6-naphthalenedicarboxylate, and low levels of particulate contaminants.

By operating according to the process of this invention highly pure DM-2,6-NDC can be prepared. In the crystallization step it is essential to cool the esterification reaction to a temperature not greater than about 40° C. thereby providing for the crystallization of a major portion of the DM-2,6-NDC and a major portion of the MM-2,6-NDC formed in the esterification reaction. After partitioning the methanol from the esterification reaction mother liquor, the resulting residue, which contains most of the undesirable impurities, can be discarded. In the process of this invention, the recrystallization step is conducted at a temperature to provide for the recrystallization of the desired DM-2,6-NDC without also crystallizing a major portion of MM-2,6-NDC. This recrystallization step, because it provides for the efficient partitioning of DM-2,6-NDC from MM-2,6-NDC, allows for the use of low ratios of methanol to 2,6-NDA in the esterification reaction. Additionally, because the majority of the undesirable impurities are removed in the crystallization step, the MM-2,6-NDC separated from the DM-2,6-NDC in the recrystallization step is relatively free of impurities and it can be recycled to the esterification reactor where it is converted to DM-2,6-NDC. Finally, for those applications requiring DM-2,6-NDC with low levels of particulate contamination, the present process provides for a vacuum distillation to remove particulates as well as impurities not removed by the crystallization and recrystallization steps.

DETAILED DESCRIPTION OF THE INVENTION

The 2,6-naphthalenedicarboxylic acid (2,6-NDA) used to prepare dimethyl-2,6-naphthalenedicarboxylate (DM-2,6-NDC) in the process of this invention can be prepared by any suitable process such as, for example, thermally disproportionating a naphthalene monocarboxylic and/or naphthalenedicarboxylic acid by the so-called "Henkel" reaction. However, from the standpoint of commercial applicability, the 2,6-NDA used to prepare DM-2,6-NDC in the process of this invention is most suitably prepared by the heavy metal catalyzed, liquid phase oxidation of a 2,6-dialkyl- or 2-alkyl-6-acyl naphthalene feedstock compound. The alkyl group in the 2,6-dialkylnaphthalene contains one to three carbon atoms and is independently selected from methyl, ethyl and isopropyl. Thus, the 2,6-dialkylnaphthalene can, for example, be 2,6-dimethylnaphthalene, 2,6-diethylnaphthalene, 2-ethyl-6-methylnaphthalene or 2,6-diisopropylnaphthalene. The alkyl group in the 2-alkyl-6-acyl naphthalene compound is also an alkyl group containing one to three carbon atoms and is selected from methyl, ethyl and isopropyl. The acyl group in the 2-alkyl-6-acyl naphthalene compound contains two to five carbon atoms. Preferably, the acyl group is acetyl, i.e., a two carbon atom acyl group. Methods for preparing 2,6-dialkylnaphthalenes and methods for preparing 2-alkyl-6-acyl naphthalenes are well known in the art. For example, in Sikkenga et al., U.S. patent applications Ser. Nos. 539,007 and 539,087, filed Jun. 15, 1990, processes for preparing 2,6-dimethylnaphthalene are disclosed; in Hagen et al., U.S. patent application Ser. No. 486,783, filed Mar. 1, 1990, processes for preparing 2-acyl-6-methylnaphthalene are disclosed, and in Hagen et al., U.S. Pat. No. 4,873,386, issued Oct. 10, 1989, processes for preparing 2,6-diethylnaphthalene are disclosed. 2,6-Dimethylnaphthalene and 2,6-diethylnaphthalene, because they are most easily prepared and are low in molecular weight, are the preferred oxidation feedstocks for the process of this invention.

The oxidation reaction used to convert the 2,6-dialkyl- or 2-alkyl-6-acyl naphthalene feedstock compound to 2,6-naphthalenedicarboxylic acid is a liquid phase reaction wherein a heavy metal catalyst comprising cobalt, manganese and bromine components are used to catalyze the oxidation of the alkyl groups and acyl groups on a given naphthalene compound to carboxylic acid groups. When the alkyl group is ethyl or isopropyl, a cerium catalyst component is also used. A source of molecular oxygen, such as air, supplies the oxygen for the oxidation reaction. The solvent for the liquid phase oxidation reaction comprises a low molecular weight aliphatic carboxylic acid having one to six carbon atoms, or a mixture of such a low molecular weight aliphatic carboxylic acid and water. Suitable solvents include acetic acid, propionic acid, n-butyric acid, water and mixtures thereof. Preferably, due to cost and availability, the oxidation solvent comprises acetic acid. More preferably, the solvent comprises a mixture of acetic acid and water. When water is used with acetic acid as the solvent, the water is suitably 1 to 20 weight percent relative to the acetic acid, as introduced into the oxidation reactor. During the oxidation reaction, heat is generated. This heat is dissipated in part by the vaporization of the solvent in the oxidation reactor. Typically, some of the vaporized solvent is withdrawn from the reactor, condensed, and then returned to the reactor. Additionally, some solvent is withdrawn from the oxidation reactor as a liquid in the product stream. After separation of the crude 2,6-naphthalenedicarboxylic acid from the product stream, at least a portion of the oxidation reaction mother liquor can be recycled to the oxidation reactor.

The source of molecular oxygen employed in the oxidation step of the process of this invention can vary in molecular oxygen concentration from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis).

In more detail, the catalyst employed in the oxidation step of the process of this invention comprises a bromine-containing component and at least one of a cobalt- and manganese-containing component, and can additionally comprise accelerators known in the art. Preferably, the catalyst comprises cobalt-, manganese-, and bromine-containing components. The weight ratio of cobalt (calculated as elemental cobalt) in the cobalt component of the catalyst to the 2,6-dialkylnaphthalene or 2-alkyl-6-acyl naphthalene in the liquid-phase oxidation is in the range of from about 0.1 to about 500 milligram atoms (mga) per gram mole of dialkylnaphthalene or 2-alkyl-6-acyl naphthalene. The weight ratio of manganese (calculated as elemental manganese) in the manganese component of the catalyst to cobalt (calculated as elemental cobalt) in the cobalt component of the catalyst in the liquid-phase oxidation is in the range of from about 0.1 to about 10 mga per mga of cobalt. When used, the weight ratio of cerium (calculated as elemental cerium) in the cerium component of the catalyst to cobalt (calculated as elemental cobalt) in the cobalt component of the catalyst in the liquid-phase oxidation is in the range of about 0.025 to about 1.0 mga per mga of cobalt. The weight ratio of bromine (calculated as elemental bromine) in the bromine component of the catalyst to total cobalt and manganese (calculated as elemental cobalt and elemental manganese) in the cobalt and manganese components of the catalyst in the liquid-phase oxidation is in the range of from about 0.05 to about 5.0 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.05:1.0 to 5.0:1.0 bromine to total cobalt and manganese milligram atom ratio is provided by a suitable source of bromine. Such bromine sources include elemental bromine ($Br_2$), or ionic bromide (e.g., HBr, NaBr, KBr, $NH_4Br$, etc.), or organic bromides which are known to provide bromide ions at the operating temperature of the oxidation (e.g., benzylbromide, mono- and di-bromoacetic acid, bromoacetyl bromide, tetrabromoethane, ethylene-dibromide, etc.). The total bromine in molecular bromine and ionic bromide is used to determine satisfaction of the elemental bromine to total cobalt and manganese milligram atom ratio of 0.05:1.0 to 5.0:1.0. The bromine ion released from the organic bromides at the oxidation operating conditions can be readily determined by known analytical means.

In operation, the minimum pressure at which the oxidation reactor is maintained is that pressure which will maintain a substantial liquid phase of the 2,6-dialkylnaphthalene or 2-alkyl-6-acyl naphthalene and at least 50 and preferably at least 70 percent of the solvent. The 2,6-dialkylnaphthalene or 2-alkyl-6-acyl naphthalene and solvent not in the liquid phase because of vaporization is removed from the oxidation reactor as a vapor-gas mixture, condensed, and then returned to the oxidation reactor. When the solvent is an acetic acid-water mixture, suitable reaction pressures in the oxidation reactor are in the range of from about 0 atmosphere absolute to about 35 atmospheres absolute, and typically are in the range of from about 10 atmospheres absolute to about 30 atmospheres absolute. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The oxidation of the process of this invention can be performed either in a batch, continuous, or semi-continuous mode. In the batch mode, the 2,6-dialkylnaphthalene or 2-alkyl-6-acyl naphthalene, solvent and the catalyst components are initially introduced batchwise into the reactor, and the temperature and pressure of the reactor contents are then raised to the desired levels to start the oxidation reaction. Air is introduced continuously into the reactor. After commencement of the oxidation reaction—for example, after all the 2,6-dialkylnaphthalene or 2-alkyl-6-acyl naphthalene has been completely introduced into the reactor—the temperature of the reactor contents is raised.

In the continuous mode, each of 2,6-dialkylnaphthalene or 2-alkyl-6-acyl naphthalene, air, solvent and catalyst are continuously introduced into the reactor, and a product stream comprising 2,6-NDA and catalyst components dissolved in the solvent is withdrawn from the reactor. In the semicontinuous mode, the solvent and catalyst are initially introduced into the reactor and then the 2,6-dialkynaphthalene or 2-alkyl-6-acyl naphthalene and air are continuously introduced into the reactor. Catalyst can also be added during the reaction. Thereafter, the product stream in the continuous mode or the reactor contents in the batch or semicontinuous mode are cooled to a temperature in the range of from about 40° C. to about 150° C. in at least one step and in at least one crystallizer such that essentially all of the 2,6-NDA crystallizes in the solvent. Following crystallization, the resulting slurry of 2,6-NDA in the mother liquor is separated, typically by centrifugation, at a temperature in the range of from about 40° C. to about 150° C. Suitably, the separation is performed at essentially the same temperature as the final crystallization temperature. Processes for oxidizing 2,6-diethyl- and 2,6-diisopropylnaphthalene are disclosed in U.S. patent application Ser. No. 557,588 filed on Jul. 24, 1990, the specification of which is hereby specifically incorporated by reference.

After the 2,6-NDA is prepared, the next step comprises converting it, by esterification with methanol, to DM-2,6-NDC. Although some impurities such as brominated 2,6-naphthalenedicarboxylic acid and other brominated compounds, 6-formyl-2-naphthoic acid (FNA), 6-methyl-2-naphthoic acid, and cobalt and manganese catalyst metals are partly removed during the process of isolating 2,6-NDA from the oxidation reaction mixture, unacceptable levels of impurities remain with the 2,6-NDA and are consequently carried over to the esterification reaction and must be removed during the purification of DM-2,6-NDC.

In the process of this invention, 2,6-NDA is converted to DM-2,6-NDC by heating 2,6-NDA with methanol at a temperature and for a time sufficient to convert at least a portion and preferably at least 50 percent and more preferably at least 75 percent of the 2,6-NDA to DM-2,6-NDC. Although other solvents can be used along with the methanol, it is presently preferred to use only methanol. This esterification reaction generates one molecule of water for each carboxylic acid moiety esterified with methanol. The weight ratio of methanol to 2,6-NDA is suitably in the range of from about 0.3:1 to about 10:1, respectively. It is most preferred, however, to use as low a weight ratio of methanol to 2,6-NDA as possible, such as about 0.3:1 to about 6:1, for a large-scale continuous process. Low ratios of methanol to 2,6-NDA allow for small esterification reactor sizes for a given throughput of 2,6-NDA, less methanol to remove from the DM-2,6-NDC product, and less methanol to recycle.

The temperature for the esterification reaction is suitably in the range of about 80° C. to about 400° C., preferably in the range of 90° C. to about 360° C. The pressure for the esterification reaction suitably ranges from about 2.0 atmospheres absolute to about 200 atmospheres absolute. Preferably, due to the low boiling point of methanol and the preferred reaction temperature of 90° C. to about 360° C., the pressure for the esterification reaction is in the range of about 3 to about 180 atmospheres absolute. It is desirable to maintain the pressure at a level sufficient to maintain at least a portion of the methanol in the liquid state. However, even where the pressure is not sufficiently high to maintain the methanol in the liquid state, the esterification reaction can occur in the liquid phase comprising liquified DM-2,6-NDC. Furthermore, DM-2,6-NDC and/or MM-2,6-NDC can be added with the esterification reactor feed to provide a liquid phase for the reaction.

The reactor used to carry out the esterification reaction can be any vessel or apparatus suitable for conducting the reaction at the desired reaction temperature and pressure. For example, the reactor can be a well-stirred batch reactor, a continuous flow-stirred tank reactor, with or without partitions, or a tubular reactor, preferably a plug-flow tubular reactor. The reactor can be equipped with suitable agitators and baffles to provide for adequate mixing. Two or more reactors in series, where the reactors are the same or different, can be used as, for example, a continuous flow-stirred tank reactor followed by a plug-flow tubular reactor.

The esterification reaction residence time in the esterification reactor is suitably in the range of about 0.01 to about 10 hours.

The esterification reaction can be conducted with or without an esterification catalyst present. When the reaction is conducted at low temperatures in the range of about 80° C. to about 200° C., a catalyst is highly advantageous. We have found that sulfuric acid is a preferred catalyst for these low reaction temperatures. Sulfuric acid suitably accelerates the esterification reaction and, of greater significance, it solubilizes residual oxidation catalyst metals contained with the DM-2,6-NDC allowing for their removal when the DM-2,6-NDC is separated from the esterification reaction mother liquor after crystallization. However, other acidic catalysts such as other inorganic acids including, for example, phosphoric acid, HF, $BF_3$ and HCl are suitable. Strong organic acids such as an aromatic sulfonic acid including benzene sulfonic acid, toluene sulfonic acid, and sulfonic acid made by sulfonating an alkylated aromatic compound are also suitable. Other strong organic acids such as methane sulfonic acid and the chloro- and fluoro-acetic acids, i.e., mono-, di- or tri-chloroacetic acid, are also suitable acidic catalysts. When used, the amount of sulfuric acid required for catalyzing the methanol esterification of 2,6-NDA and solubilizing the residual oxidation catalyst metals is about 2 to about 25, and preferably about 4 to about 16 weight percent based on the weight of 2,6-NDA charged to the esterification reaction zone. When the esterification reaction is conducted at high temperatures, i.e., temperatures in the range of about 200° C. to about 400° C., a catalyst is optional. If a catalyst is used, an acidic catalyst such as an inorganic acid or strong organic acid is suitable, particularly those mentioned above. However, when a strongly acidic esterification catalyst is used for the high temperature esterification reaction, it is necessary to use highly corrosion resistant and expensive materials of construction for the esterification reactor. Also, unless they can be recycled, acidic esterification catalysts present disposal problems for high volume operations. Presently preferred is to use a metal-based esterification catalyst for the high temperature esterification reaction. These are generally nonacidic or low in acidity. Highly corrosion resistant materials of construction are not required for the esterification reactor when these metal-based catalysts are used. Their elimination from the esterification reaction product mixture and subsequent disposal, if necessary, is also simplified because of the lower amounts used. Suitable metal-based esterification catalysts include molybdenum compounds such as a molybdenum halide, cyanide, thiocyanide, oxyhalide, carboxylic acid salt, oxide, sulfide, oxysulfide or oxysulfate; a molybdic, phosphomolybdic or silicomolybdic acid; or a sodium, potassium, or ammonium molybdate, phosphomolybdate or silicomolybdate; an oxide, hydroxide, carbonate, halide or carboxylic acid of cobalt or manganese; titanium compounds such as a titanium III (or IV) sulphate, titanyl sulfate, titanium trichloride, and titanate esters such as tetra-n-butyl titanate or tetra-iso-propyl titanate; zinc and zinc compounds such as zinc halides or zinc oxide; and organotin compounds such as monobutyltin oxide hydride, butylchlorotin dihydroxide and monobutyltin tris(2-ethylhexanoate). A selection of suitable metal esterification catalysts is disclosed in British Patent Specification 1,437,897. Molybdenum trioxide, zinc, zinc oxide, titanate esters and organo tin compounds are the preferred metal-based esterification catalysts.

When a metal-based esterification catalyst is used, it is present in the esterification reaction mixture in an amount in the range of about 0.01 to about 5 weight percent based on the weight of 2,6-NDA charged to the esterification reaction mixture.

The esterification reaction product mixture typically comprises a mixture of DM-2,6-NDC and MM-2,6-NDC, excess methanol, water, organic impurities, esterification catalyst (if used), and residual oxidation catalyst metals. Because the DM-2,6-NDC is more soluble in methanol than 2,6-NDA, the DM-2,6-NDC is in solution in the hot esterification reaction mixture. The MM-2,6-NDC is also typically in solution. The residual oxidation catalyst metals, however, are to a certain extent insoluble in the esterification reaction product mixture. In the presently preferred process for obtaining purified DM-2,6-NDC, these catalyst metals must be removed prior to the downstream distillation step. It is convenient to remove these oxidation catalyst metals from the esterification reaction product mixture immediately after the esterification reaction while the reaction mixture is still hot and the DM-2,6-NDC and MM-2,6-NDC are still in solution. If they are not removed, the oxidation catalyst metals are incorporated in the DM-2,6-NDC as the DM-2,6-NDC crystallizes from the esterification reaction product mixture upon cooling. Any suitable means for removing the insoluble oxidation catalyst metals from the esterification reaction product mixture can be used. For example, centrifugation, filtration (particularly pressure filtration) or settling are suitable means. However, the most preferred method is to use one or more liquid cyclones, commonly called hydroclones, to remove these solids. Hydroclones operate without moving parts and do not require filter beds or centrifuge baskets that necessitate periodic cleaning and/or replacement. Bottoms exiting the hydroclones (or the centrifuged, settled or filtered matter) are concentrated in oxidation catalyst metals and can be recycled to the oxidation reaction. As previously mentioned, if the oxidation catalyst metals are permitted to remain in the DM-2,6-NDC purification process stream, they concentrate in either the distillation bottoms, and, if the DM-2,6-NDC is injected into the distillation column at a point within the distillation column packing, the oxidation catalyst metals will rapidly and possibly irreversibly plug the distillation column. Also, when oxidation catalyst metals are allowed to concentrate in the distillation bottoms, they can produce a highly viscous material that is not easily removed by, for example, a purge stream. Periodic cleaning would therefore necessitate the discontinuance of the distillation process. Furthermore, it is desirable to recycle to the esterification reactor at least part and preferably substantially all of the distillation bottoms to recover any DM-2,6-NDC and/or MM-2,6-NDC contained therein. If the catalyst metals are not removed, they will only increase in concentration in the distillation bottoms with recycle and aggravate the aforementioned problems. As discussed hereinabove, when sulfuric acid is used as the esterification catalyst, the sulfuric acid solubilizes the oxidation catalyst metals and they are not incorporated in the crystallized DM-2,6-NDC.

After the esterification reaction is completed, the esterification reaction mixture is cooled to crystallize the 2,6-NDA esters, i.e., DM-2,6-NDC and MM-2,6-NDC, contained therein. The cooling can be accomplished by any suitable means. However, the cooling is most efficiently accomplished by a pressure reduction with the consequent evaporation of methanol cooling the esterification reaction mixture. This can be accomplished in one zone, or it can be accomplished in a series of cooling zones. In a batch mode operation, the esterification reaction vessel can be used to crystallize the 2,6-NDA esters. Although the temperature to which the esterification reaction mixture is cooled is variable and depends, in part, upon the ratio of methanol to 2,6-NDA used in the esterification reaction and the desired degree to which the 2,6-NDA esters are to be crystallized from the methanol, the esterification reaction mixture must be cooled to a temperature not greater than about 40° C., preferably to a temperature in the range of about 10° C. to about 30° C., and most preferably to a temperature of about 20° C. Cooling the reaction mixture to these temperatures can be suitably accomplished by subjecting the esterification reaction mixture to a vacuum, thereby accelerating evaporative cooling and achieving temperatures below the normal boiling point of methanol. All or part of the evaporated methanol may be condensed by cooling and returned to the crystallization vessel. Other suitable methods for cooling the mixture can be used, however. Cooling the reaction mixture to these temperatures assures that a major portion of the 2,6-NDA esters crystallize from solution. Preferably at least about 75 percent and more preferably at least about 90 percent of the 2,6-NDA esters contained in the esterification reaction mother liquor crystallize from solution.

After the 2,6-NDA esters crystallize, they are partitioned from the esterification reaction mother liquor. This can be accomplished by any suitable means for partitioning solids from liquids such as those described above for separating the oxidation catalyst metals from the esterification reaction mixture. A rotary vacuum filter, however, is a particularly suitable means for conducting this partitioning. Unreacted 2,6-naphthalenedicarboxylic acid, if present, also precipitates during the cooling and is collected with the 2,6-NDA esters.

With the esterification reaction mother liquor are rejected most of the impurities such as brominated products, esterified FNA, solubilized catalyst metals (if sulfuric acid is used as the esterification catalyst), water produced in the esterification reaction, and yet unidentified oxidation and esterification reaction intermediates and reaction side products. The esterification reaction mother liquor is, however, mainly unreacted methanol used for the esterification reaction. This methanol can be recovered from the mother liquor and used for recycle to one or more of the other process steps. The methanol, as a mixture with water produced in the esterification reaction, is separated (stripped) from the mother liquor using any suitable method. The water is then typically separated from the methanol using a distillation apparatus such as a distillation tower with trays. The bottoms produced from this stripping operation are highly concentrated in the aforementioned oxidation and esterification reaction impurities and are typically discarded, although at least a portion can be recycled to either the esterification or oxidation reactor.

Crystallized 2,6-NDA esters collected on the filter, centrifuge basket, or that obtained from some other means used for partitioning the crystallized product from the esterification reaction mother liquor, are preferably washed with methanol, mixtures of methanol and water, or other suitable solvent such as a $C_5$-$C_{10}$ hydrocarbon, i.e., pentanes, hexanes, toluene, xylenes, cyclohexane, etc. A $C_6$-$C_{10}$ halogenated aromatic such as chlorobenzene, or a $C_1$-$C_4$ carboxylic acid such as acetic and propionic acid, and mixtures of these acids with water are also suitable solvents for washing the crystallized esters. This washing step removes additional impurities and results in purer DM-2,6-NDC, particularly if the solvent used to wash the 2,6-NDA esters is at an elevated temperature. Most preferably, the solvent used to wash the crystallized 2,6-NDA esters is methanol, or a mixture of methanol and water. Used methanol or methanol/water washes can conveniently be treated in a manner similar to the esterification reaction mother liquor for recovery of the methanol. The weight ratio of solvent, preferably methanol or methanol/water mixture, to the 2,6-NDA esters used to wash the esters is in the range of about 0.2:1 to about 2:1, respectively.

The crystallized product mixture of DM-2,6-NDC and MM-2,6-NDC, which may contain from about 2 to about 20 percent by weight of MM-2,6-NDC, and more typically about 2 to about 10 weight percent MM-2,6-NDC, is subjected to a recrystallization procedure for further purification. Recrystallization is accomplished by contacting the 2,6-NDA esters with methanol or other suitable recrystallization solvent and maintaining the resulting recrystallization mixture at an elevated temperature to dissolve at least a portion of the DM-2,6-NDC and preferably at least 75 percent and more preferably at least 90 percent of the DM-2,6-NDC. Substantially all of the MM-2,6-NDC, for example, at least about 90 percent and preferably at least about 95 percent of the MM-2,6-NDC in the crystallized 2,6-NDA esters is also dissolved. A pressure vessel can be used to heat the mixture to a temperature above the normal boiling point of the solvent. Suitable weight ratios of recrystallization solvent to 2,6-NDA esters are in the range of about 1:1 to about 10:1, and preferably about 2:1 to about 6:1, respectively, by weight. Methanol is the presently preferred recrystallization solvent because it is used in the esterification reaction and it can be treated and recycled along with other methanol process streams. These amounts of methanol are generally sufficient to dissolve the 2,6-NDA esters at reasonable temperatures and provide a recrystallized product suitable for the next stage of purification. However, as mentioned above, other recrystallization solvents are suitable. For example, $C_6$-$C_{10}$ aromatic solvents such as benzene, toluene, o-, m- or p-xylene, a mixture of xylenes, ethylbenzene, cumene, pseudocumene, and the like, are suitable as recrystallization solvents. Halogenated $C_1$-$C_{10}$ aromatic solvents such as chlorobenzene are also suitable. The preferred temperature for dissolving the 2,6-NDA esters in the recrystallization solvent is in the range of about 80° C. to about 190° C. It is also possible that esterification of MM-2,6-NDC occurs during the dissolution when methanol is used as the solvent.

After the 2,6-NDA esters and the recrystallization solvent are maintained at an elevated temperature so that substantially all of the MM-2,6-NDC and at least a portion of the DM-2,6-NDC are dissolved, the resulting mixture is cooled to a recrystallization temperature to recrystallize the dissolved DM-2,6-NDC while maintaining a major portion of the MM-2,6-NDC in solution in the recrystallization mother liquor, for example, at least 50 percent and more preferably at least 75 percent of the MM-2,6-NDC originally in the 2,6-NDA esters remains in solution. Cooling is accomplished by any suitable means; however, it is preferable from the standpoint of cost in a plant operation to reduce the pressure and allow the mixture to cool by evaporative cooling. If the dissolution of the 2,6-NDA esters in the recrystallization solvent is accomplished at temperatures above the normal boiling point of the recrystallization solvent, the pressure need only be reduced to lower the temperature of the mixture. However, attaining temperatures below the normal boiling point of the solvent by evaporative cooling requires the application of a vacuum to the vessel or apparatus holding the recrystallization solution. The recrystallization temperature is any temperature that allows for the recrystallization of at least a portion of the DM-2,6-NDC, and preferably at least about 75 percent and more preferably at least about 90 percent of the DM-2,6-NDC, while maintaining a major portion of the MM-2,6-NDC in solution. When methanol is the recrystallization solvent, the recrystallization temperature must be at least about 45° C. and preferably in the range of about 45° C. to about 120° C., more preferably about 55° C. to about 80° C., and most preferably about the normal boiling point of methanol, i.e., 65° C. We have determined that the MM-2,6-NDC is soluble in the methanol recrystallization solvent at these temperatures. This solubility provides for the recrystallization of DM-2,6-NDC with substantially reduced levels of MM-2,6-NDC. Necessarily, a portion of the DM-2,6-NDC also remains in solution at these high temperatures, however, the mother liquor containing the MM-2,6-NDC and non-recrystallized DM-2,6-NDC can be recycled to the esterification reaction resulting in reduced or no loss of product.

Additionally, we have determined that the recrystallization of DM-2,6-NDC from methanol at the aforementioned recrystallization temperatures of at least about 45° C. provides for a more effective separation of the methyl ester of FNA from DM-2,6-NDC. The reason for this is uncertain, however, one explanation is that the methyl ester of FNA co-crystallizes with DM-2,6-NDC in a temperature-dependent manner such that relative to DM-2,6-NDC more methyl ester of FNA co-crystallizes with the DM-2,6-NDC at a lower recrystallization temperature than at the aforementioned higher recrystallization temperatures.

This ability to cool the recrystallization solvent to a temperature that recrystallizes a major amount of the desired DM-2,6-NDC while leaving a major portion of the MM-2,6-NDC in solution is highly significant for the overall process of preparing high purity DM-2,6-NDC. The MM-2,6-NDC, if permitted to crystallize along with the DM-2,6-NDC, is conveyed to the distillation step in the process where, because MM-2,6-NDC is a high melting solid and is significantly less volatile than DM-2,6-NDC, it concentrates in the distillation bottoms and precipitates and fouls the distillation column and/or distillation column reboiler. Also, because MM-2,6-NDC is the major high boiling component in the DM-2,6-NDC feed to the distillation column, its removal allows for a distillation bottoms stream that is more concentrated in the non-usable, high boiling components of the DM-2,6-NDC distillation feed. Disposal of concentrated bottoms wastes lesser amounts of the valuable MM-2,6-NDC.

The step of this process wherein the recrystallization mixture of DM-2,6-NDC is cooled to recrystallize the DM-2,6-NDC while leaving a major portion of the MM-2,6-NDC in solution also provides a significant amount of flexibility for the esterification reaction. In the esterification reaction, the amount of MM-2,6-NDC formed is necessarily a function of the ratio of methanol to 2,6-NDA fed to the esterification reactor. Reaction residence time, catalyst concentration and reaction temperature are, of course, important factors contributing to the rate at which equilibrium is achieved; however, for an esterification reaction allowed to reach equilibrium, the amount of MM-2,6-NDC present will be a function of the methanol to 2,6-NDA ratio because of the following equilibria:

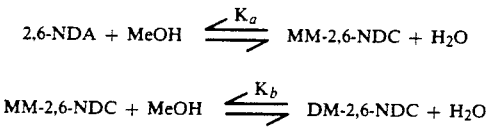

$$2,6\text{-NDA} + \text{MeOH} \underset{}{\overset{K_a}{\rightleftharpoons}} \text{MM-2,6-NDC} + H_2O$$

$$\text{MM-2,6-NDC} + \text{MeOH} \underset{}{\overset{K_b}{\rightleftharpoons}} \text{DM-2,6-NDC} + H_2O$$

Therefore, in order to produce a maximized concentration of DM-2,6-NDC at equilibrium, a large molar excess of methanol (MeOH) is required.

Esterification reaction mixtures wherein the ratio of methanol to 2,6-NDA is high necessarily means the reaction volume is large. The large reaction volume requires a large reactor for conducting the esterification reaction. Due to the high cost of large reactors, particularly large pressure reactors, the use of a high ratio of methanol to 2,6-NDA necessitates a large expenditure for the esterification reactor. A preferred approach is to use a lower ratio of methanol to 2,6-NDA, preferably in the range of about 0.3:1 to about 6:1 by weight, respectively. Although an increased amount of MM-2,6-NDC will be formed, a considerably smaller reactor can be used. A high concentration of MM-2,6-NDC in the DM-2,6-NDC, for example, up to 20 weight percent, can be accommodated in the present process because the hereinabove discussed recrystallization step separates MM-2,6-NDC from the DM-2,6-NDC for recycle to the esterification reactor before the MM-2,6-NDC enters the distillation apparatus. Thus, this process provides for the flexibility of using a variety of methanol to 2,6-NDA ratios, a flexibility that can be used to vary the size and type of the esterification reactor to suit specific needs.

Upon recrystallization of the solid DM-2,6-NDC, it is partitioned from the recrystallization solvent (mother liquor) by any suitable means for partitioning solids from liquids such as, for example, settling, centrifugation, vacuum or pressure filtration, etc. If the partitioning of the recrystallized DM-2,6-NDC from the recrystallization solvent is conducted at a temperature near or above the normal boiling point of the recrystallization solvent, a pressure filter apparatus is the preferred means for effecting the separation. Generally, the temperature at which the recrystallized DM-2,6-NDC is partitioned from the recrystallization solvent is about the same as the hereinabove described recrystallization temperature. As mentioned above, if methanol is used as a solvent, the filtrate can be recycled to the esterification reactor. Alternatively, it can be treated to remove the methanol and the remaining heavies can be recycled to the esterification reactor or discarded. If a solvent other than methanol is used as the recrystallization solvent, it too can be treated to remove heavies and then purified for reuse. Solid recrystallized DM-2,6-NDC collected on the filter, centrifuge, etc. is preferably washed, preferably with the solvent used for the recrystallization step, or other suitable solvent such as those discussed hereinabove used to wash the crystallized 2,6-NDA esters. Washing removes additional impurities particularly if the washing solvent is at an elevated temperature. The weight ratio of solvent to DM-2,6-NDC used to wash the recrystallized DM-2,6-NDC is suitably in the range of about 0.2:1 to about 2:1, respectively. Depending on variables such as the amount of time the DM-2,6-NDC remains in the centrifuge, vacuum filter, pressure filter or other partitioning device, the pressure (or vacuum) applied, and the solvent used for recrystallization and/or washing, etc., the DM-2,6-NDC filter cake will contain variable amounts of solvent. This solvent can, if desired, be removed by one or more drying techniques such as heating in a sweep of air or inert gas, use of a vacuum with or without additional heating, or other suitable means for drying the DM-2,6-NDC. Presently preferred, however, is to heat the DM-2,6-NDC, optionally at reduced pressure, until it becomes molten and simultaneously distilling any excess solvent from the DM-2,6-NDC. Molten DM-2,6-NDC, preferably free of substantially all of the solvent used for the recrystallization and/or washing, is distilled in the next step of the process. Although only one recrystallization step has been described, it will be apparent to those of skill in the art that, depending on the degree of purity required, one or more additional recrystallization procedures, with or without a washing step and using the same or different recrystallization and washing solvents, can be used. Additionally, while the DM-2,6-NDC is in solution in the recrystallization solvent, it can be treated with one or more physical or chemical means for stabilizing the DM-2,6-NDC or for removing impurities. For example, it can be treated with an oxidizing agent such as air, a peroxide, hydroperoxide or peracid. It can be treated with a reducing agent. It can also be treated with a base such as an alkoxide, e.g., sodium methoxide, or calcium, sodium or potassium hydroxide, carbonate or bicarbonate.

Molten recrystallized ester is distilled in at least one distillation step. Due to the high melting point of DM-2,6-NDC (approximately 190° C.), the temperature of the distillation is necessarily above about 190° C. Also, because DM-2,6-NDC deteriorates in purity, and particularly in color, by being maintained at excessive temperatures, it is preferable to conduct the distillation at reduced pressure. Distillation tower bottoms are therefore suitably in the range of about 190° C. to about 310° C., preferably about 210° C. to about 290° C. Distillation pressure can range from about 2.5 torr to about 200 torr. Preferably, the distillation pressure is in the range of about 6 to about 100 torr.

The distillation can be a simple distillation, however, to attain the highest purity of DM-2,6-NDC, it is preferable to use a fractionating column. The fractionating column can be packed with random or structured column packing designed to increase the liquid-vapor contact in the column. Fractionation columns having trays, e.g. sieve trays or bubble cap trays, which are well known in the distillation art, are also suitable.

Distillation of the DM-2,6-NDC removes undesirable light or lower boiling impurities such as methanol, the methyl ester of 2-naphthoic acid and trimethyltrimellitate. It also removes heavy high boiling impurities, such as residual MM-2,6-NDC, various colored by-products, and residual catalyst metals. Importantly, the distillation removes particulate contaminants from the DM-2,6-NDC. Particulate contaminants that range in size down to 1.5 microns are difficult to remove from the DM-2,6-NDC unless a distillation step is employed. For example, even if the DM-2,6-NDC is dissolved in a suitable solvent, filtered and recrystallized, the solid DM-2,6-NDC must be collected by, for example, filtration or centrifugation and is also usually dried to free the DM-2,6-NDC of excess recrystallization solvent. These operations introduce particulate contaminants into the DM-2,6-NDC. Consequently, the distillation procedure of this invention as the final purification procedure assures that the DM-2,6-NDC contains low levels of particulate contaminants, levels that are suitable for manufacturing PEN that can be used for fabricating high quality thin films. Preferably, the distillation step provides for DM-2,6-NDC containing less than about 5000 and more preferably less than about 2000 particles per gram, wherein the particles are greater than about 1.5 microns in size and wherein a HIAC/ROYCO instrument is used for the particle analysis.

The vacuum system providing the low pressure for the fractionation column is exposed to fractionation column overhead vapor that contains low levels of vaporized DM-2,6-NDC. If permitted to enter the vacuum system, the DM-2,6-NDC in the overhead vapor would condense as a solid and eventually plug the vacuum system. A means to overcome this problem is to scrub the overhead vapors with methanol chilled to a temperature such that the vapor pressure of the methanol is low. The resulting slurry of methanol and scrubbed DM-2,6-NDC is recycled to a point in the process upstream of the fractionation column. Scrubbing with chilled methanol provides for the efficient removal of vaporized DM-2,6-NDC without introducing any additional compounds to the process streams. The chilled methanol is at a temperature in the range of about 0° C. to about the freezing point of methanol, i.e. −93° C. For example, a temperature of about −15° C. is suitable.

We have also determined that the location where the molten DM-2,6-NDC enters the fractionation column can be adjusted to avoid plugging of column packing. Although the disclosed process includes steps to remove heavy, high boiling or non-volatile impurities from the DM-2,6-NDC before the DM-2,6-NDC is distilled, the DM-2,6-NDC nevertheless contains some of these heavy impurities. In a continuous process where the DM-2,6-NDC is fed to a continuous fractionation column containing a structured packing, these heavies will, in time, collect in an eventually plug the column. For the continuous distillation of a product such as DM-2,6-NDC where a major part of the feed is taken overhead in a highly purified form, one would normally introduce the feed at a point intermediate between the top and bottom of the fractionation column, i.e. within the structured packing, to achieve a bottom stream concentrated in the heavy impurities. However, we have determined that DM-2,6-NDC can be introduced at a point below the structured column packing in a continuous distillation and, contrary to expectations, an excellent separation of the heavies from the desired DM-2,6-NDC was achieved resulting in concentrated distillation bottoms. In contrast, when the continuous distillation was conducted by adding the same DM-2,6-NDC feed at a location within the column packing, a relatively rapid increase in pressure at the bottom of the column resulted indicating that the column packing was plugging. The advantage gained in operability by introducing the DM-2,6-NDC feed below the column packing greatly exceeds any reduction in column efficiency that may result.

Another means for preventing the accumulation of catalyst metals and other heavies in the fractionation column is to conduct a preliminary distillation to separate the non-volatile, very heavy impurities from the DM-2,6-NDC. This is conveniently accomplished using methanol vapor as the heat source to volatilize the DM-2,6-NDC. Hot methanol, rather than some other heat source, has less of a tendency to cause thermal degradation of the DM-2,6-NDC. The vapor containing the vaporized DM-2,6-NDC and methanol is cooled sufficiently to remove most of the DM-2,6-NDC and maintain the methanol as a vapor. The condensed DM-2,6-NDC is directed to the fractionation column, while the methanol is recycled.

Additionally, the distillation bottoms produced in the distillation of DM-2,6-NDC can be treated to remove insoluble heavies contained therein. For example, a slip-stream can be taken from a reboiler loop used to supply heat to the fractionating column. This slip-stream can be discarded, recycled to the esterification reactor, or treated to remove insoluble heavies and then either recycled to the esterification reactor or returned to the reboiler loop. For example, insoluble matter in the slip-stream can be removed by filtration or centrifugation. Alternatively, the slip-stream can be directed to one or more hydroclones to separate insolubles from the liquid distillation bottoms. Overflow from the hydroclones can be returned to the reboiler loop or it can be recycled to the esterification reactor. The overflow can be discarded or processed further and recycled to, for example, the oxidation reactor.

It is to be understood that the hereinabove described process for preparing purified DM-2,6-NDC can be conducted in a manner such that each process step is separately operated in either a batch or continuous manner. For a large-scale, commercial operation, it is most suitable to conduct the entire process in a continuous manner wherein the herein described process steps are conducted in series-arranged reaction and process zones.

The following examples are being presented to facilitate an understanding of the process of the present invention without intending to limit the scope thereof.

In the following Examples, "MeFNA" is the methyl ester of 2-formyl-6-naphthoic acid.

YIE measurements and APHA color measurements were used to evaluate the color of DM-2,6-NDC. "Ambient" YIE values for the samples of DM-2,6-NDC were measured on a Gardner XL-835 tri-stimulus colorimeter using quartz sample cells. YIE measurements were taken on a 0.75 gram sample of DM-2,6-NDC dissolved in 25 ml. of chloroform (see ASTM method E-313, "Indexes of Whiteness and Yellowness of Near-White, Opaque Materials"). YIE values referred to as "Air Melt" were similarly measured using samples that were first maintained at 235° C. for six hours in a glass vessel without excluding air, i.e., the "Air Melt" measurements are an indication of the stability of the DM-2,6-NDC sample to air at an elevated temperature.

APHA (American Public Health Assoc.) color values were measured using molten samples of DM-2,6-NDC.

Delta Y values were measured by passing a solution of 20 g of DM-2,6-NDC in 1000 ml of dichloromethane through 47 mm diameter filter paper and measuring the "Y" value of the filter paper using a Gardner XL-835 tri-stimulus colorimeter. Delta Y is a measure of particulate contamination in the DM-2,6-NDC.

Particulate contamination in the DM-2,6-NDC was also measured using a HIAC/ROYCO particle analyzer. A methylene chloride solution of DM-2,6-NDC was used for the measurements. This instrument measures particles greater than 1.5 microns in size.

EXAMPLE I

A batch esterification of 2,6-NDA was carried out in a 25-gallon autoclave made of 316 stainless steel and equipped with magnetic stirrer, heater, cooling coil, and thermocouple. The 2,6-NDA was prepared by the cobalt, manganese and bromine catalyzed liquid-phase oxidation of 2,6-dimethylnaphthalene. The autoclave was charged with 8165 g crude 2,6-NDA, 32660 g methanol and 10.6 g molybdenum trioxide. The mixture was heated with agitation to 256° C. and held at that temperature for one hour. It was then cooled to 25° C. and filtered using a pressure filter. The cake was washed with 16560 g methanol and dried. The dried cake weighed 6388 g. The low yield is explained by the fact that some product adhered to the wall of the autoclave. An analysis of the crude DM-2,6-NDC by liquid chromatography showed 1.18 percent 2,6-NDA, 10.28 percent MM-2,6-NDC and 0.0234 percent MeFNA, by weight. An X-ray fluorescence analysis showed 57 ppm bromine. A one-liter autoclave made of 316 stainless steel and equipped with a heater, magnetic stirrer and thermocouple was charged with 330.7 g methanol and 110.25 g of this crude DM-2,6-NDC and MM-2,6-NDC. The DM-2,6-NDC and MM-2,6-NDC were dissolved by heating with agitation to 154° C. The mixture was then cooled to 21° C. to recrystallize the DM-2,6-NDC. The resulting slurry was filtered, and the cake was washed with 163.2 g methanol and dried. The weight of the dried cake was 105.94 g, and an analysis by liquid chromatography showed 0.89 percent 2,6-NDA, 9.28 percent MM-2,6-NDC and 0.0070 percent MeFNA, by weight. An X-ray fluorescence analysis showed 24 ppm bromine.

EXAMPLE II

A one-liter autoclave made of 316 stainless steel and equipped with heater, magnetic stirrer and thermocouple was charged with 330.7 g methanol and 110.71 g crude DM-2,6-NDC and MM-2,6-NDC, having the same analysis as given in Example I. The DM-2,6-NDC and MM-2,6-NDC were dissolved by heating with agitation to 154° C. The mixture was then cooled to 65° C. (the normal boiling point of methanol) to recrystallize the DM-2,6-NDC. The resulting slurry was filtered using a steam-heated funnel, and the cake was washed with 165.7 g boiling methanol and dried. The weight of the dried cake was 99.59 g, and an analysis by liquid chromatography showed 0.65 percent 2,6-NDA, 3.88 percent MM-2,6-NDC and 0.0020 percent MeFNA, by weight. An X-ray fluorescence analysis showed 15 ppm bromine.

A comparison of Example I with Example II shows that the higher recrystallization and filtration temperature was much more effective in reducing MM-2,6-NDC and MeFNA and was also more effective in reducing 2,6-NDA and bromine in the DM-2,6-NDC.

EXAMPLE III

Two batch esterifications were carried out in a 25-gallon autoclave made of 316 stainless steel and equipped with magnetic stirrer, heater, cooling coil, and thermocouple. The autoclave was charged with 8210 g crude 2,6-NDA, 32890 g methanol and 10.6 g molybdenum trioxide. The crude 2,6-NDA was prepared by the cobalt, manganese and bromine catalyzed liquid-phase oxidation of 2,6-dimethylnaphthalene and contained 0.28 ppm 6-formyl-2-naphthoic acid (FNA) and 2050 ppm bromine. The mixture was heated with agitation to 255° C. and held at that temperature for 15 minutes. It was then cooled to 23° C. and filtered using a pressure filter. The cake was washed with 16330 g methanol and dried. The dried cake weighed 8564 g. An analysis of the filter cake by liquid chromatography showed 1.26 percent 2,6-NDA, 9.55 percent MM-2,6-NDC and 0.0238 percent MeFNA, by weight.

A second esterification was run in the same autoclave using 8165 g 2,6-NDA, 32,660 g methanol and 10.6 g molybdenum trioxide. The mixture was heated with agitation to 265° C. and held at that temperature for 15 minutes. It was then cooled to 33° C. and filtered using a pressure filter. The cake was washed with 16330 g methanol and dried. The dried cake weighed 7660 g, and an analysis by liquid chromatography showed 0.86 percent 2,6-NDA, 7.28 percent MM-2,6-NDC and 0.0278 percent MeFNA, by weight. The low yield is believed to be due to some of the product adhering to the autoclave wall.

For the recrystallization step, the autoclave was charged with 6804 g dry cake from the first esterification, 7711 g dry cake from the second esterification, and 47630 g methanol. The DM-2,6-NDC and MM-2,6-NDC were dissolved by heating to 140° C. The mixture was cooled to 69° C. to recrystallize the DM-2,6-NDC. The resulting slurry was filtered using a pressure filter which had been preheated to 69° C. For the washing step, 18320 g of methanol were charged to the autoclave, heated to 69° C., and passed through the filter cake. The washed cake was dried. The dried cake weighed 13949 g. An analysis by liquid chromatography showed 0.51 percent 2,6-NDA and 1.44 percent MM-2,6-NDC and 0.0008 percent MeFNA by weight. Bromine was 7 ppm.

The dried recrystallized DM-2,6-NDC was purified by continuous distillation using a 3" ID column equipped with heated feed system, wiped-film evaporator, reflux splitter, heated distillate take-off system, and vacuum pump. The column was packed with 78" Sulzer CY TM packing, a high-efficiency structured packing made of 316 stainless steel gauze. The feed was introduced into the column below the packing. The column pressure was maintained at 40 torr. The feed rate was 48.0 g/min, and the reflux ratio was 1.5:1. A distillate product was removed at the rate of 34.0 g/min. The product was white and contained no detectable 2,6-NDA or MM-2,6-NDC, 0.0019 ppm MeFNA, and less than 2 ppm bromine. The APHA color was 66.

The example demonstrates that DM-2,6-NDC having low color and low levels of impurities such as 2,6-NDA, MM-2,6-NDC, MeFNA and bromine can be prepared by the process of this invention wherein recrystallized DM-2,6-NDC is subjected to vacuum distillation. This example also demonstrates that the recrystallization step of this invention greatly reduces the level of MM-2,6-NDC and MeFNA in the crude DM-2,6-NDC.

EXAMPLE IV

Crude 2,6-NDA was esterified with methanol utilizing sulfuric acid catalyst in a batch process. The 2,6-NDA was prepared by the cobalt, manganese and bromine catalyzed liquid-phase oxidation of 2,6-dimethylnaphthalene. A glass-lined reactor was charged with 130 parts crude 2,6-NDA as a slurry in 1140 parts methanol and 13 parts, 80 percent sulfuric acid. (The other 20% is water.) The reactor was equipped with an overhead condenser and 150 psig rupture disc. The mixture was heated, utilizing a steam jacket, until the reactor internals reached approximately 120° C. The esterification mixture was maintained at 120° C. for a six hour period after which the reactor was slowly cooled overnight with a water jacket. The crude ester was isolated from the mother liquor using a perforated basket centrifuge. The product was isolated in four separate centrifuge cycles and each centrifuge cake was washed with 50 parts methanol. The crude ester (minus 10 parts for sample retain) was recrystallized in 1050 parts methanol in the same glass-lined reactor. The mixture was heated until dissolution, held at 120° C. for 30 minutes and slowly cooled to ambient temperature overnight. The recrystallized DM-2,6-NDC was isolated in three centrifuge cycles and washed with 50 parts methanol. The wet recrystallized cake was dried in an explosion-proof tray oven. A summary of the analyses of the crude 2,6-NDA crude DM-2,6-NDC, and recrystallized DM-2,6-NDC (131 parts) is presented in Table I.

The recrystallized material was purified by batch distillation. The apparatus consisted of a heated one-liter reboiler flask; a 1" ID column filled with 34" of a high-efficiency structured gauze packing; an overhead condenser cooled with tempered oil; a reflux splitter; a condensate receiver; and a vacuum pump protected by a water-cooled cold trap. The product takeoff system was enclosed in a box heated to about 230° C. to prevent freezing of the distillate.

Prior to the distillation, the unit was washed with boiling xylene. Dry recrystallized DM-2,6-NDC (493.2 g) was then distilled at a pressure of 20 torr. The product was recovered as three fractions weighing 157.6; 157.7; and 123.7 grams, respectively. The water trap contained 0.50 gram of solid material. A distillation pot residue of water-like fluidity with no visible solids and weighing 17.74 g (3.60 percent of the feed) was obtained. The total recovery was 92.7 weight percent based on the feed. Typically about 5–10 percent of the charge is held up in the distillation unit, presumably mostly in the packing.

Table II shows that the product was of excellent quality. There was no detectable sulfur in the product, not even in the first cut. The trap material contained 40 ppm sulfur, but its contribution on a weight basis is very small. The acidity of all distillates was extremely low. Bromine, organic contaminants, and color were very low. Importantly, the use of sulfuric acid as the catalyst for the esterification provided for the removal of oxidation catalyst metals. The resulting distillation pot residue was fluid and solids-free.

TABLE I

Analytical Results for Crude 2,6-NDA Esterification and Recrystallization

|  | 2,6-NDA | Crude DM-2,6-NDC | Recrystallized DM-2,6-NDC |
|---|---|---|---|
| FNA$^a$ (ppm)$^b$ | 5212 | ND | ND |
| MeFNA$^a$ (ppm) | NA | 296 | 29 |
| MM2,6-NDC$^a$ (ppm) | NA | 11000 | 1795 |
| 2,6-NDA (ppm) | NA | ND | ND |
| Bromine$^c$ (ppm) | 1264 | 40 | 15 |
| Ash (ppm) | 1585 | 10 | 10 |
| Sulfur$^d$ (ppm) | NA | 67 | 31 |
| Acid Number (mg KOH/gram) | NA | 2.97 | 0.05 |

NA = Not Applicable
ND = Not Detected
$^a$Determined by liquid chromatography.
$^b$Parts per million
$^c$Determined by x-ray fluorescence.
$^d$Determined couloumbmetrically.

TABLE II

| Sample | Feed | Dist. Cuts 1–3 | Dist. Cuts 4–6 | Dist. Cuts 7–9 | Total Dist. | Bottoms | Trap |
|---|---|---|---|---|---|---|---|
| Sample Wt., g | 493.2 | 157.6 | 157.7 | 123.7 | 439.0 | 17.74 | 0.50 |
| CONC$^a$, ppm: | | | | | | | |
| Br | 15 | 5 | <2 | <2 | <3 | 127 | NA |
| Co | <2 | <2 | <2 | <2 | <2 | 104 | NA |
| Fe | <2 | <2 | <2 | <2 | <2 | 61 | NA |
| Mn | <2 | <2 | <2 | <2 | <2 | 63 | NA |
| Sulfur$^b$, ppm | 31 | <1 | <1 | <1 | <1 | NA | 40 |
| YIE (Ambient) | NA | 0.02 | 0.01 | 0.01 | 0.01 | NA | NA |
| YIE (Air Melt) | 27.2 | 0.19 | 0.17 | 0.13 | 0.17 | NA | NA |
| Delta Y | NA | 1.62 | 0.84 | 0.29 | 0.97 | NA | NA |
| Acid No. mg KOH/g | 0.050 | 0.01 | <0.01 | <0.01 | <0.01 | NA | NA |
| GC$^c$, ppm: | | | | | | | |
| MeFNA | NA | 40 | <20 | <20 | <27 | NA | NA |
| Unknowns | NA | 90 | <20 | <20 | <45 | NA | NA |
| LC$^d$, ppm: | | | | | | | |
| 2,6-NDA | | 4 | 2 | 4 | 3 | 2450 | NA |
| MM-2,6-NDC | 1800 | 3 | 1 | 3 | 2 | 67,300 | NA |

TABLE II-continued

| Sample | Feed | Batch Distillation Results Dist. Cuts 1–3 | Dist. Cuts 4–6 | Dist. Cuts 7–9 | Total Dist. | Bottoms | Trap |
|---|---|---|---|---|---|---|---|
| MeFNA | 29 | 48 | 10 | 8 | 23 | 43 | NA |

NA = Not Available
[a]Determined by X-ray fluorescence.
[b]Determined couloumbmetrically.
[c]Gas chromatography, parts per million by weight.
[d]Liquid chromatography, parts per million by weight.

EXAMPLE V

According to the procedure of Example IV, crude 2,6-naphthalenedicarboxylic acid (2,6-NDA) was esterified, and the resulting crude dimethyl-2,6-naphthalenedicarboxylate (DM 2,6-NDC) was recrystallized and dried.

The recrystallized material was purified by continuous distillation. The apparatus consisted of a heated feed tank on a scale, a feed control valve, a 3" ID column filled with 78" of Sulzer CY TM packing; a wiped-film evaporator; a residue receiver, a reflux splitter, an overhead condenser cooled with tempered oil, a condensate receiver, and a vacuum pump protected by two cold traps. The column and the product takeoff system were enclosed in an insulated box heated to about 230° C. to prevent freezing of the distillate.

The feed was introduced above the evaporator and below the packing at a rate of 60.5 g/min. The reflux ratio was 1:1; and the pressure at the reflux splitter was maintained at 20 torr. The average distillate and residue rates were about 43.9 and 16.6 g/min., respectively. Table III shows the product analyses. Product colors by both the YIE and APHA methods were very low. Particulate contents measured by the HIAC-Royco instrument were also very low. DM-2,6-NDC prepared by procedures similar to that used to prepare the feed DM-2,6-NDC for this example as well as by other procedures were also measured for particulate levels prior to distillation. The particulate concentrations for these samples ranged from 46,900 particles/gram to 175,000 particles/gram. Therefore, this example demonstrates that distillation effectively provides for DM-2,6-NDC having very low levels of particulate contamination.

TABLE III

| Cut No. | Continuous Distillation of Methanol-Recrystallized DM 2,6-NDC (Feed) | 1 | 2 | 3 | 4 | 5 | 6 |
|---|---|---|---|---|---|---|---|
| Br[a], ppm | 11 | <2 | <2 | <2 | NA | <2 | <2 |
| APHA Color | NA | 51 | 62 | 86 | NA | 72 | 62 |
| Delta Y | NA | 0.5 | 0.3 | 0.3 | NA | 0.3 | 0.9 |
| Haze (NTU) | NA | 0.04 | 0.05 | 0.04 | NA | 0.05 | 0.04 |
| YIE (Air Melt) | NA | 0.10 | 0.08 | 0.11 | NA | 0.10 | 0.08 |
| Acid No. mg KOH/g | NA | <0.01 | <0.01 | <0.01 | NA | <0.01 | 0.01 |
| Particles >1.5 microns[b] | NA | 1837 | 1625 | 839 | NA | 676 | 1391 |
| LC, ppm: | | | | | | | |
| 2,6-NDA | NA | <4 | <4 | <4 | NA | <4 | <4 |
| MM 2,6-NDA | 785 | 2 | 2 | 4 | NA | <2 | 4 |
| MeFNA | ND | 17 | 15 | 14 | NA | 17 | 19 |

NA = Not Available
[a]Determined by X-ray fluorescence.
[b]Particles greater than 1.5 microns in size per gram of DM-2,6-NDC, measured with a HIAC/Royce instrument.

EXAMPLE VI

Recrystallized DM-2,6-NDC containing 2.28 percent 2,6-NDA, 3.53 percent MM-2,6-NDC, 0.053 percent cobalt, 0.78 percent manganese and 0.048 percent molybdenum was batch distilled at 20 torr. The distillation was terminated when the bottoms temperature reached 288° C. (i.e. 30° C. above the boiling point of pure DM-2,6-NDC at 20 torr.). At this point, 82.3 percent of the feed had distilled over, and 17.8 percent of the feed was recovered as bottoms. The material in the bottoms was a semi-solid that did not flow even at 315° C. The viscosity, measured with a Brookfield instrument, exceeded 2,000,000 cps. A material of this viscosity could not be pumped except with an extruder or similar device. The formation of this material in the distillation bottoms is, therefore, unacceptable for commercial operations. The cobalt, manganese and molybdenum in the feed for this distillation was present because procedures were not used to remove these metals from the esterification reaction mixture. In similar distillations, such as Example IV, where the metals were not present in the distillation feed because sulfuric acid was used as an esterification catalyst, the highly viscous bottoms residue did not form.

EXAMPLE VII

The solubility of MM-2,6-NDC in methanol was measured at various temperatures as shown below. Additionally, it was observed that MM-2,6-NDC tends to form a supersaturated solution in methanol solvent.

| Solubility of MM-2,6-NDC (g/100 g methanol) | Temperature °C. | (°F.) |
|---|---|---|
| 0.096 | 9.4 | (49) |
| 0.255 | 30.6 | (87) |
| 0.510 | 51.7 | (125) |
| 0.744 | 55.0 | (131) |
| 1.493 | 80.3 | (177) |
| 2.811 | 108.3 | (227) |
| 8.917 | 143.9 | (291) |

While only certain embodiments have been set forth, alternative embodiments and various modifications will be apparent from the above description to those skilled in the art. These and other alternatives are considered equivalents and within the spirit and scope of the present invention.

We claim:

1. A process for the improved recovery of dimethyl-2,6-naphthalenedicarboxylate from a reaction mixture comprising methanol, dissolved dimethyl-2,6-naphthalenedicarboxylate and dissolved mono-methyl-2,6-naphthalenedicarboxylate which process comprises:
    a) crystallizing a major portion of the dissolved dimethyl-2,6-naphthalenedicarboxylate and mono-methyl-2,6-naphthalenedicarboxylate by cooling the reaction mixture to a temperature not greater than about 40° C.; b) partitioning reaction mixture mother liquor from crystallized dimethyl-2,6-naphthalenedicarboxylate and mono-methyl-2,6-naphthalenedicarboxylate; c) heating partitioned dimethyl-2,6-naphthalenedicarboxylate and mono-methyl-2,6-naphthalenedicarboxylate in a recrystallization solvent at a temperature sufficient to dissolve at least a portion of the dimethyl-2,6-naphthalenedicarboxylate and substantially all of the mono-methyl-2,6-naphthalenedicarboxylate; d) recrystallizing dimethyl-2,6-naphthalenedicarboxylate dissolved in the solvent at a temperature to recrystallize the dimethyl-2,6-naphthalenedicarboxylate while maintaining a major portion of the mono-methyl-2,6-naphthalenedicarboxylate in recrystallization mother liquor; and e) partitioning recrystallized dimethyl-2,6-naphthalenedicarboxylate from the recrystallization mother liquor to form recrystallized dimethyl-2,6-naphthalenedicarboxylate.

2. The process of claim 1 wherein the reaction mixture in step a) is cooled to a temperature in the range of about 10° C. to about 30° C.

3. The process of claim 1 wherein the recrystallizing in step d) is carried out at a temperature in the range of about 45° C. to about 120° C. and the recrystallization solvent is methanol.

4. The process of claim 3 wherein partitioned mother liquor in step e) is recycled to the reaction mixture prior to step a).

5. The process of claim 1 wherein prior to step c) crystallized dimethyl-2,6-naphthalenedicarboxylate and mono-methyl-2,6-naphthalenedicarboxylate partitioned from the mother liquor are washed with a solvent.

6. The process of claim 5 wherein the solvent is methanol.

7. The process of claim 1 wherein partitioned recrystallized dimethyl-2,6-naphthalenedicarboxylate is washed with a solvent.

8. The process of claim 1 wherein residual solvent in the recrystallized dimethyl-2,6-naphthalenedicarboxylate is removed by heating the dimethyl-2,6-naphthalenedicarboxylate until it is molten and simultaneously distilling the residual solvent.

9. The process of claim 1 wherein dimethyl-2,6-naphthalenedicarboxylate and mono-methyl-2,6-naphthalenedicarboxylic acid dissolved in recrystallization solvent in step c) is treated with at least one physical or chemical means to remove impurities.

10. The process of claim 1 practiced continuously.

11. A process for the improved recovery of dimethyl-2,6-naphthalenedicarboxylate from a reaction mixture comprising methanol, dissolved dimethyl-2,6-naphthalenedicarboxylate and dissolved mono-methyl-2,6-naphthalenedicarboxylate which process comprises:
    a) crystallizing a major portion of the dissolved dimethyl-2,6-naphthalenedicarboxylate and mono-methyl-2,6-naphthalenedicarboxylate by cooling the reaction mixture to a temperature not greater than about 40° C.; b) partitioning reaction mixture mother liquor from crystallized dimethyl-2,6-naphthalenedicarboxylate and mono-methyl-2,6-naphthalenedicarboxylate; c) heating partitioned dimethyl-2,6-naphthalenedicarboxylate and mono-methyl-2,6-naphthalenedicarboxylate in methanol at a temperature sufficient to dissolve at least a portion of the dimethyl-2,6-naphthalenedicarboxylate and substantially all of the mono-methyl-2,6-naphthalenedicarboxylate; d) recrystallizing dimethyl-2,6-naphthalenedicarboxylate dissolved in the methanol at a temperature of at least about 45° C. while maintaining a major portion of the mono-methyl-2,6-naphthalenedicarboxylate in recrystallization mother liquor; e) partitioning recrystallized dimethyl-2,6-naphthalenedicarboxylate from the recrystallization mother liquor to recover recrystallized dimethyl-2,6-naphthalenedicarboxylate; and f) vacuum distilling recrystallized dimethyl-2,6-naphthalenedicarboxylate to form highly purified dimethyl-2,6-naphthalenedicarboxylate.

12. The process of claim 11 wherein the vacuum distilling is conducted using a fractionation column packed with structured packing.

13. The process of claim 11 wherein the vacuum distilling is conducted using a fractionation column equipped with a chilled methanol scrubber to remove residual dimethyl-2,6-naphthalenedicarboxylate from column overhead vapors.

14. The process of claim 11 wherein the 2,6-naphthalenedicarboxylic acid is prepared by the liquid phase oxidation of a 2,6-dialkyl- or 2-alkyl-6-acyl naphthalene compound using molecular oxygen and catalyzed by a catalyst comprising cobalt, manganese and bromine components.

15. The process of claim 14 wherein insoluble residual oxidation catalyst metals comprising cobalt and manganese contained in the reaction mixture are removed from the reaction mixture prior to step a).

16. The process of claim 15 wherein at least one liquid cyclone is used to remove the insoluble oxidation catalyst metals from the reaction mixture.

17. The process of claim 11 wherein distillation bottoms produced during the vacuum distilling are treated to remove insoluble material during the distillation.

18. The process of claim 17 wherein the insoluble material is removed from the distillation bottoms using a liquid cyclone.

19. The process of claim 11 wherein prior to step f) the recrystallized dimethyl-2,6-naphthalenedicarboxylate is pre-distilled to separate the dimethyl-2,6-naphthalenedicarboxylate from non-volatile impurities in the recrystallized dimethyl-2,6-naphthalenedicarboxylate.

20. The process of claim 19 wherein hot methanol vapor contacted with the recrystallized dimethyl-2,6-naphthalenedicarboxylate is used to volatilize the dimethyl-2,6-naphthalenedicarboxylate during the pre-distillation.

* * * * *